(12) United States Patent
Mizuno

(10) Patent No.: US 6,307,072 B2
(45) Date of Patent: Oct. 23, 2001

(54) METHOD FOR PRODUCTION OF OXYGEN-CONTAINING ORGANIC COMPOUND

(75) Inventor: Noritaka Mizuno, Tokyo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/746,158

(22) Filed: Dec. 22, 2000

(30) Foreign Application Priority Data

Dec. 24, 1999 (JP) .................................................. 11-366542
Nov. 8, 2000 (JP) .................................................. 12-340760

(51) Int. Cl.$^7$ ................................................. C07D 301/12
(52) U.S. Cl. .............................................................. 549/531
(58) Field of Search ............................................... 549/531

(56) References Cited

U.S. PATENT DOCUMENTS

| | | | |
|---|---|---|---|
| 2,608,534 | 8/1952 | Fleck | 252/435 |
| 4,833,260 | 5/1989 | Neri et al. | 549/531 |
| 6,087,513 | * 7/2000 | Liao et al. | 549/524 |
| 6,103,915 | * 8/2000 | Arca et al. | 549/531 |
| 6,160,137 | * 12/2000 | Tsuji et al. | 549/523 |
| 6,160,138 | * 12/2000 | Escrig et al. | 549/531 |
| 6,194,591 | * 2/2001 | Grey et al. | 549/533 |
| 6,225,482 | * 5/2001 | Drauz et al. | 549/525 |

FOREIGN PATENT DOCUMENTS

| | | | |
|---|---|---|---|
| 0 100 119 B1 | 9/1986 | (EP) . | |
| 0 596 859 A2 | 5/1994 | (EP) | B01J/27/186 |
| 0 620 205 A1 | 10/1994 | (EP) | C07C/53/08 |
| 0 623 386 A2 | 11/1994 | (EP) | B01J/23/64 |
| 0 782 979 A1 | 7/1997 | (EP) | C07C/67/36 |
| 2 764 211 | 12/1998 | (FR) | B01J/23/85 |
| 40-26184 | 11/1965 | (JP) . | |
| 54132519 A | 10/1979 | (JP) . | |
| 62234550 A | 10/1987 | (JP) . | |
| 04169576 A | 6/1992 | (JP) . | |
| 04352771 A | 12/1992 | (JP) . | |
| 08-213917 | 8/1993 | (JP) . | |
| 08-038909 | 2/1996 | (JP) . | |
| 08-127550 | 5/1996 | (JP) . | |
| 2000-212116 | 8/2000 | (JP) . | |
| WO 97/47614 | 12/1997 | (WO) . | |
| WO 98/54165 | 12/1998 | (WO) . | |

OTHER PUBLICATIONS

Groves et al., "Aerobic Epoxidation of Olefins with Ruthenium Porphyrin Catalysts", J. am. Chem. Soc. 107:5790–5792, 1985.

Neumann et al., "A Ruthenium–substituted Polyoxometalate as an Inorganic Dioxygenase for Activation of Molecular Oxygen", Nature 388:353–355, 1997.

Takai et al., "Aerobic Epoxidation of Olefinic Compounds Catalyzed By Tris(1,3–diketonato)iron(III)", Bull. Chem. Soc. Jpn 64:2513–2518, 1991.

\* cited by examiner

*Primary Examiner*—Deborah C. Lambkin
(74) *Attorney, Agent, or Firm*—Fish & Richardson P.C.

(57) ABSTRACT

A novel method for the production of an oxygen-containing organic compound is provided. The production of an oxygen-containing organic compound is attained by oxidizing an olefin, an alcohol, or an aldehyde by catalyzing thereof with a molecular oxygen-containing gas in the presence of a catalyst formed of a polyoxo metalate substituted with a divalent transition metal cation.

12 Claims, 1 Drawing Sheet

METHOD FOR PRODUCTION OF OXYGEN-CONTAINING ORGANIC COMPOUND

BACKGROUND OF THE INVENTION

1. Field of the Invention

This invention relates to a catalyst for the production of an oxygen-containing compound and to a method for the production of an oxygen-containing compound. More particularly, It relates to a catalyst intended for producing an oxygen-containing compound by oxidizing an olefin, an alcohol, or an aldehyde with a polyoxo metalate substituted with a transition metal and serving as a catalyst in the presence of a molecular oxygen-containing gas and to a method for producing the oxygen-containing organic compound. still more specifically, it relates to a catalyst for producing an epoxide compound by oxidizing an olefin, a carbonyl compound by oxidizing an alcohol, or a carboxylic acid by oxidizing an aldehyde and to a method for producing the catalyst.

2. Description of the Related Art

The reaction of oxidation is one of the important and basic reactions in the industry of organic chemistry. Generally, the method of nitric acid oxidation using nitric acid as an oxidizing agent is most widely known. Since this method entails emission of $N_2O$ and $NO_x$, however, it necessitates the attachment to the reaction vessel of an extra device intended to remove such nitrogen oxides. As other oxidizing agents, chromic acid and manganese compounds are well known. Since the method of interest uses such a metal compound in a large amount, it also necessitates an after-treatment such as recovery. Now that particularly the problems of natural resources and environment are attracting attention, the conventional method reveals itself to have room for further improvements When the reaction of oxidation is enabled to be directly effected by using molecular oxygen or air as an oxidizing agent in the presence of a catalyst, therefore, a fair method of production can be afforded. Since the activation of oxygen generally requires a high temperature and a high pressure, no high selectivity can be hoped for in the production aimed at. Thus, for the purpose of alleviating the reaction conditions, it has been proposed to use an alcohol or an aldehyde as a co-oxidizing agent or a reducing agent. This proposed use is still problematic because it entails by-production of a relevant aldehyde or organic acid.

JP-A-08-38,909 and JP-A-2000-212,116 disclose a method for producing a ketone, an aldehyde, an organic carboxylic acid, etc. by the oxidation with oxygen under comparatively mild reaction conditions, with a specific imide compound such as N-hydroxyphthal imide used as a main catalyst. This method, however, cannot be rated as excellent because the imide compound catalyst discharging the role of a radical generating agent is decomposed or wasted during the course of the reaction and because the amount of the catalyst to be used is large relative to the substrate for reaction is unduly large. A method which, in the production of glycolic acid by the oxidation of ethylene glycol with an oxygen-containing gas, uses a catalyst incorporating a lead compound in platinum and/or platinum is disclosed in JP-A-54-132,519. This method, however, ought to supply the reaction system with an alkali and naturally suffers the carboxylic acid to transform into an alkali salt and, therefore, needs to give the reaction system a treatment for neutralization and desalination.

To cite the reaction for epoxidizing an olefin, for example, the fact of synthesizing an epoxide by adding one oxygen atom to a carbon-carbon double bond constitutes itself one of the important methods of chemical conversion. The epoxide is often utilized as an intermediate compound which can be converted into an end product. The reaction for epoxidizing an olefin can be implemented by numerous techniques. The oldest and most general method for this reaction consists in having an olefin react with an organic peracid (as taught, for example, in JP-A-04-169,576). Typical peracids are perbenzoic acid, peracetic acid, and the like. The salts of such acids also serve as effective oxidizing agents. This method of reaction, however, entails several defects. The first of the defects resides in the fact that the reaction of epoxide with water and/or the acid in the reaction solvent is liable to form such by-products as a glycol and a glycol ester. The second thereof resides in the fact that the by-produced acid must be recovered or recycled And the third thereof resides in the fact that since the reaction uses an organic peracid, it must be controlled strictly from the viewpoint of ensuring safety.

Methods for effecting an expected oxidation with hydrogen peroxide or an organic hydroperoxide by using a compound containing Ti (IV), V (V), Mo (VI), or W (VI) or titanosilicate as a catalyst with a view to lessening the danger caused with a peracid have been proposed (the official gazettes of JP-B-40-26,184 and BP 100,119). The hydroperoxides which are generally used for such reactions are tertiary butyl peroxide, cumene peroxide, ethyl benzene peroxide, and the like. These reactions are safe because the reactants used therein have low reactivity as compared with the organic peracids. They nevertheless are liable to induce (such secondary reactions as) a reaction of displacement at the allylic position of an olefin and a reaction of oxidation in the place of the addition of oxygen to the double bond.

Where a compound containing Ti (IV), V (V), Mo (VI), or W (VI) or titanosilicate in used as a catalyst and the aqueous solution of hydrogen peroxide is used as an oxidizing agent, the process forms water as a by-product and, therefore, brings a tender effect on the environment and obviates the necessity for recovery or recyclization. When hydrogen peroxide is used additionally, titanium silicate (TS-1), titanium-substituted zeolite (disclosed, for example, in EP 100,119, WO 9747614, and 4,833,260), and various heteropoly acids (disclosed, for example, in JP-A-62-234, 550) are used as effective and selective catalysts.

In many cases, the aqueous solution of hydrogen peroxide is used as an ideal oxidizing agent where the reaction is selective. Unfortunately, however, the formed epoxide is caused by water to encounter ring opening and suffer from a decline in yield. There are times when the hydrogen peroxide becomes relatively expensive when the price of the epoxide is low.

Incidentally, the ideal oxidizing agent for the epoxidization of an olefin is ecologically and economically the molecular oxygen (dioxidine) which exists in the air. The addition of dioxidine to an olefin is thermodynamically unfavorable and requires a catalyst. The basic problem that confronts the use of dioxidine for the epoxidization of an olefin consists in the fact that the molecular oxygen is possessed of a radical quality. In a homogeneous reaction, this radical quality infallibly induces a radical reaction preferentially through the route of the displacement of the hydrogen atom attached to the carbon atom at the allylic position. The use of a dioxidine in a catalytic reaction performed in a liquid phase, therefore, encounters difficulty in obtaining an epoxide as a main product.

Recently, as a major trend of the development of such reactions of oxidation, numerous catalyst systems which, by activating oxygen in the presence of a reducing agent and effecting a reaction of the in vivo mono-atomic oxygen adding enzyme type under comparatively mild conditions, are enabled to manifest high selectivity despite low activity have been proposed. Conceptually, the use of molecular oxygen in the reaction of epoxidization of an olefin ought to necessitate the formation of a metal oxo compound of high valency which occurs after the cleavage of an oxygen-oxygen bond. The metal oxo intermediate or such high valency serves as an effective epoxidizing agent. For the purpose of effecting the reaction of expxidization of an olefin by the cleavage of an oxygen-oxygen bond, however, the formation of an active metal oxo intermediate of high valency generally requires extraction of two electrons from the reducing agent. An example of obtaining in a high yield an epoxide by the reaction of epoxidization of an olefin by using an alcohol or an aldehyde as an electron donor is reported (Bull. Chem. Soc. Jpn., 1991, 64, 2513). This reaction is not favorable because it forms an aldehyde or an acid at the same time. An example of using hydrogen as a reducing agent has also been reported. JP-A-04-352,771 discloses a method for producing propylene oxide by the reaction of propylene with hydrogen and oxygen in the presence of a catalyst formed of a metal of Group VIII in the Periodic Table of the Elements and a crystalline titanosilicate. Japanese Patent No. 2,615,432 discloses a method for producing an epoxide by the oxidation with oxygen of an unsaturated hydrocarbon in the presence of molecular oxygen, hydrogen, and a catalyst containing gold and titanium dioxide. These methods invariably are problematic because they produce an epoxide in low yield and require to use dangerous and expensive hydrogen.

Besides, the mechanism of the dioxinase type is capable of activating molecular oxygen without requiring the presence of active hydrogen. In this reaction, the molecular oxygen is cleaved by using two metal cores and enabled to form two metal oxo species of high valency. An example of using a Ru-substituted tetramesytyl porphyrin [J. Am. Chem. Soc., 107, 5790 (1985)] may be cited. This catalyst, however, manifests unusually low activity to the epoxide and exhibits no perfect stability thermally in an atmosphere of oxygen.

JP-A-05-213,917 discloses a method for producing an epoxide compound by oxidizing an olefin compound with molecular oxygen in the presence of a catalyst formed of the onium salt of a heteropoly acid having tungsten as a poly atom or a derivative thereof without requiring use of such a reducing agent as hydrogen, i.e. an electron doner. This reaction produces an epoxide still in low yield.

An example of epoxidizing an olefin by using molecular oxygen as an oxidizing agent in the presence of a transition metal-substituted polyoxo metalate serving as a catalyst has been known. WO98/54165 discloses transition metal polyoxo metalate $[WZnRu_2(ZnW_9O_{19})_2]_{11}$ as a catalyst. The same inventor reports the same catalyst system in Nature, Vol. 388, Jul. 24 1997, pages 353–355. The report clearly describes that the hydroxylation of an alkane catalytically proceeds and that the hydroxylation of adamantane, for example, has 100 as the number of turnovers and the epoxidization of an alkene does not proceed catalytically under standard conditions.

An object of this invention, therefore, is to provide a novel catalyst for the production of an oxygen-containing organic compound and a novel method for the production of the oxygen-containing organic compound.

Another object of this invention is to provide a method for producing an oxygen-containing organic compound safely and economically in satisfactorily high yield from an olefin, an alcohol, or an aldehyde by using molecular oxygen as an oxidizing agent for the production of intetest.

Still another object of this invention is to provide a novel catalyst for producing an epoxide compound by the oxidation of an olefin, a carbonyl compound by the oxidation of an alcohol, or a carboxylic acid by the oxidation of an aldehyde and a novel method for the production of such a compound.

SUMMARY OF THE INVENTION

The objects mentioned above are accomplished by the following items (1)–(12).

(1) A catalyst formed of a polyoxo metalate substituted with a divalent transition metal cation and used for the production of an oxygen-containing organic compound by catalyzing an olefin, an alcohol, or an aldehyde with a molecular oxygen-containing gas.

(2) A catalyst formed of a polyoxo metalate substituted with two transition metal cations, the cations being displaced with mutually adjoining transition metal cations, and used for the production of an oxygen-containing organic compound by catalyzing an olefin, an alcohol, or an aldehyde with a molecular oxygen-containing gas.

(3) A catalyst formed of a heteropoly silicotungstate substituted with a transition metal cation and used for the production of an oxygen-containing organic compound by catalyzing an olefin, an alcohol, or an aldehyde with a molecular oxygen-containing gas.

(4) A catalyst set forth in any of the items (1)–(3) mentioned above, wherein the transition metal cation mentioned above is at least one divalent cation selected from the group consisting of manganese, iron, cobalt, and nickel.

(5) A catalyst set forth in any of the items (1)–(3) mentioned above, wherein the transition metal cation mentioned above is at least one divalent cation selected from among noble metal ions.

(6) A catalyst set forth in the item (5) mentioned above, wherein the metal cation is a ruthenium ion.

(7) A method for the production of an oxygen-containing organic compound, which comprises oxidizing an olefin, an alcohol, or an aldehyde by catalyzing thereof with a molecular oxygen-containing gas in the presence of a catalyst formed of a polyoxo metalate substituted with a divalent transition metal cation.

(8) A method for the production of an oxygen-containing organic compound, which comprises oxidizing an olefin, an alcohol, or an aldehyde by catalyzing thereof with a molecular oxygen-containing gas in the presence of a catalyst formed of a polyoxo metalate substituted with two transition metal cations, the cations being displaced with mutually adjoining transition metal cations.

(9) A method for the production of an oxygen-containing organic compound, which comprises oxidizing an olefin, an alcohol, or an aldehyde by catalyzing thereof with a molecular oxygen-containing gas in the presence of a catalyst formed of a heteropoly silicotung state substituted with a transition metal cation possessed of a γ-type Keggin structure.

(10) A method set forth in any of the items (7)–(9) mentioned above, wherein the transition metal cation mentioned above is at least one divalent cation selected from the group consisting of manganese, iron, cobalt, and nickel.

(11) A method set forth in any of the items (7)–(9) mentioned above, wherein the transition metal cation mentioned above is at least one divalent cation selected from among noble metal cations.

(12) A method set forth in the item (11) mentioned above, wherein the metal cation is a ruthenium ion.

It has been found amazingly that the use of the catalyst contemplated by this invention, though allowing the reaction of epoxidization of an olefin compound to proceed preferentially, enables a compound unpossessing a double bond such as, for example, cyclohexanol to form cyclohexanone through the oxidation of a hydroxyl group into a carbonyl group or a compound possessing a carbonyl group such as, for example, propionaldehyde to be converted into propionic acid possessing a carboxyl group.

A In the production of an oxygen-containing organic compound in accordance with the method using the catalyst of this invention by the contact of an olefin, an alcohol, or an aldehyde with molecular oxygen, the use of a catalyst formed of polyoxo metalate substituted with the cation of a divalent transition metal enables this production of the oxygen-containing organic compound to be effected safely and economically in satisfactory high yields.

EXPLANATION OF THE PREFERRED EMBODIMENTS

Figure 1:
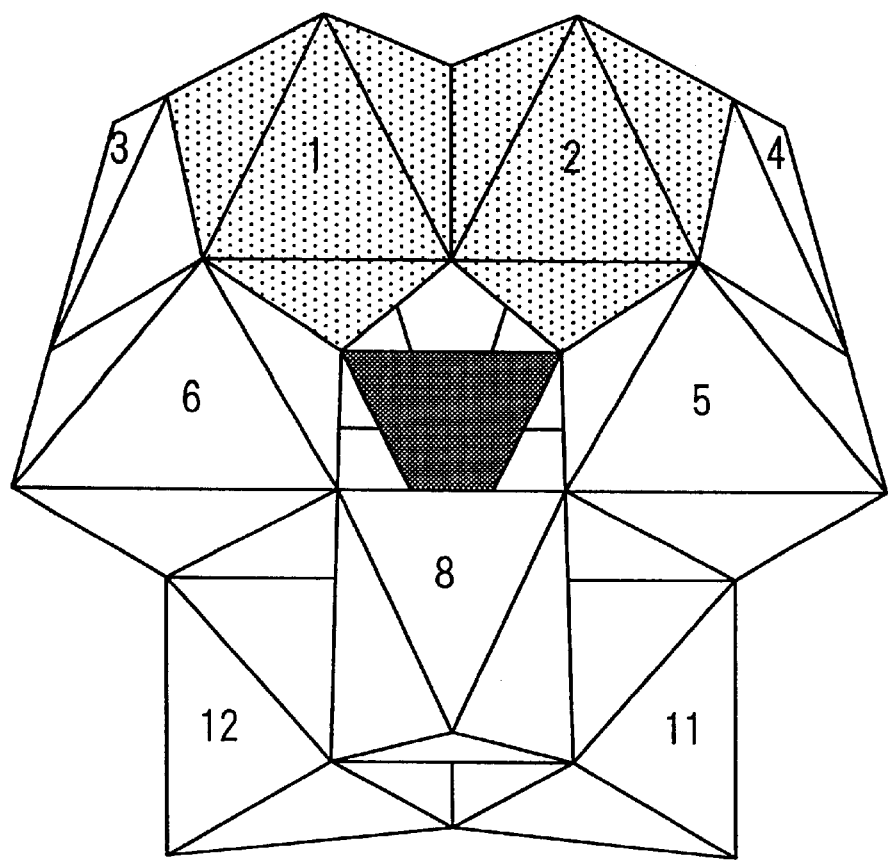
FIG. 1 illustrates the molecular structure of a typical transition metal polyoxo metalate $[\gamma\text{-SiW}_{10}\{TS\}_2O_{38})]^{q-}$.

The polyoxo metalate involved in this invention is a monomeric oxide possessing a structure defined based on tungsten, molybdenum, niobium, or vanadium, or a coordinated metal combining them. More specifically, the transition metal-substituted polyoxo metalate is a compound possessing a defectively configured Keggin structure represented by the general formula, $X_a(TS)_bM_mO_c^{q-}$. In this formula, X represents a hetero element such as, for example, silicon, phosphorus, boron, or arsenic, preferably silicon. M represents molybdenum, tungsten, niobium, or vanadium, or element combining them, preferably tungsten. TS represents the cation of a substituted transition metal in the catalyst of this invention, i.e. one species or more different species of divalent transition metal cation. Properly, it is the cation of a noble metal element selected from the group consisting of ruthenium, rhodium, palladium, osmium, iridium, and platinum, preferably a ruthenium cation. Other transition metals are Mn, Fe, Ni, Cr, Ti, 2r, Cu, V, Sm, Eu, Yb, w, and Mo, preferably the cations respectively of Mn, Fe, Co, and Ni. then, a represents an integer of 1, b an integer of 1, 2, or 3, preferably 2, and c an integer of 37, 38, or 39, preferably 38, m represents 9, 10, or 11, preferably 10, and q represents what is decided by the kinds and numbers of X and M elements.

The metalate $[\gamma\text{-SiW}_{10}\{TS\}_2O_{38})]^{q-}$ which is one example of the catalyst to be used in this invention is a defectively configured Keggin structure, wherein the TS elements are present at the position of $WO_6$ which inherently assumes two octahedral structures and the TS elements are in mutually adjoining state. The substituted TS elements are divalent cations. The structural formula is illustrated in FIG. 1 to facilitate comprehension thereof. The defectively configured Keggin type structure is known in gamma, delta, and epsilon forms of isomeric structures, particularly preferably the form of gamma structure. The TS transition metal cation in the catalyst is present at the terminal and is coordinated with such an unstable ligand as water. This is, for example, one of the active species for the formation of an epoxide from an olefin by molecular oxygen. The TS is indicated with a shaded octahedron. The $WO_6$ octahedron is indicated with an empty octahedron. The $SiO_2$ is indicated with a solid tetrahedron at the center. The Wn represents the number based on the IUPAC of the $WO_6$ in the Keggin structure.

Thus, this invention is aimed at providing a method for producing from an olefin, an alcohol, and an aldehyde compound corresponding oxygen-containing organic compounds by using a polyoxo metalate of a defectively configured Keggin structure substituted with the cation of a divalent transition metal.

The counter cations that can be used for the polyoxo metalate substituted with the transition metal mentioned above include proton, alkali metal cations, alkaline earth metal cations, transition metal cations, guaternary ammonium ion salts, quaternary phosphonium ion salts, and organic cations such as quaternary arsen, for example. The catalyst according to this invention offers stable resistance to heat and to an oxidizing atmosphere, persists stably even in an atmosphere of oxygen at temperatures at least up to the neighborhood of 200° C. as measured by differential thermal analysis, and defies decomposition even at 250° C. in dichloroethane as a solvent. The catalyst can be repeatedly used in successive rounds of one same reaction, This repetitive use of the catalyst, for example, may be effected by separating the reaction product at the end of a round of the reaction, replenishing the residual solution containing the catalyst with a new supply of the substrate for reaction, and then continuing the reaction.

The method of oxidation contemplated by this invention comprises causing the substrate for reaction to contact a molecular oxygen-containing gas in the presence of the catalyst. The reaction can be carried out in a homogeneous liquid phase system obtained by dissolving the catalyst and the substrate for reaction in a typical solvent. The typical solvent to be used herein is preferably water or generally an organic solvent inert to the reaction. As typical examples of the organic solvent, organic acids such as acetic acid and propionic acid, nitriles such as acetonitrile, acetamide, and dimethyl formamide, unsubstituted aromatic hydrocarbons such as benzene, aliphatic hydrocarbons such as hexane and octane, halogenated hydrocarbons such as chloroform, dichloromethane, dichloroethane, and chlorobenzene, nitro compounds such as nitrobenzene and nitromethane, eaters such as ethyl acetate and butyl acetate, ethers such as dimethyl ether and tetrahydrofuran, and mixtures thereof may be cited. Further, the substrate for reaction may serve as a solvent. The weight ratio of the solvent to the substrate for reaction is selected from the range of 1:10 to 1000:1, preferably from the range of 1:1 to 100:1. The catalyst, when necessary, may be suspended in the liquid phase instead of being dissolved in the solvent. It is permissible to use a heterogeneous reaction system which contains the catalyst in a solid phase and the reactants in a gaseous phase. For example, the catalyst is deposited on a carrier or it is used in a solid state such that it is enabled to incorporate therein the substrate for reaction. The carriers which are usable herein for the catalyst are various kinds of ion-exchange resin, silica, alumina, and other oxides which are generally used for heterogeneous contact reactions.

The amount of the catalyst of this invention to be used is such that the molar ratio of the catalyst to the substrate for reaction falls in the range of 1:1 to 1:1,000,000, preferably in the range of 1:1 to 1:100,000.

The olefins as the substrate for reaction in this invention include alkene compounds of 2–20 carbon atoms, preferably 3–15 carbon atoms, such as, for example, ethylene, propylene, butenes, butadienes, 1-hexene, 1-pentene, 1-heptene, 1-octane, and 1-dodecene. The alkenes include inner and branched alkenes such as, for example, 2-butene, 2-octene, 2-methyl-2-hexane, and 2,3-dimethyl-2-butene. Such cyclic olefins as, for example, cyclohexene, cylooctene, and norbornene are also included. The other olefin compounds include allenes, esters, ethers, ketones, aldehydes, nitriles, carboxylic acids, and nitro compounds which contain a carbon-carbon-double bond. Further, amines, thiols, sulfides, and disulfides which contain a carbon-caron double bond are included. Besides, the compounds of Se, Te, Sb, and As which contain a carbon-carbon double bond and the phosphines which contain a carbon-carbon double bond are included.

The alcohols as the substrate for reaction in this invention include aliphatic monohydric alcohols of 1–20 carbon atoms, preferably 1–15 carbon atoms such as, for example, methanol, ethanol, 1-propanol, isopropanol, 1-butanol, isobutanol, pentanols, 1-hexanol, 1-octanol, higher alcohols like 1-decanol, and 1-dodecanol, unsaturated aliphatic monohydric alcohols such as allyl alcohol, crotonaldehyde, and propagil alcohol, aliphatic polyhydric alcohols such as ethylene glycol, propylene glycol, trimethylene glycol, 1,2-butane diol, 1,3-butane diol, 1,4-butane diol, bexane diol, and glycerin, alicyclic monohydric alcohols ouch as cyclobutanol, cyclopentanol, cyclohexanol, methylhexanol, and cyclopentanol, alicyclic alcohols such as 1,2-cyclohexane diol, and heterocyclic alcohols such as furfuryl alcohol.

As typical examples of the aldehyde, saturated aliphatic aldehydes such as formaldehyde, acetaldehyde, propionaldehyde, butyl aldehyde, hexanal, and octaldehyde, unsaturated aldehydes such as acrolein and methacrolein, aliphatic polyaldehydes of 2–15 carbon atoms, preferably 2–10 carbon atoms ouch as glyoxal, and heterocyclic aldehydes such as furfural may be cited. The various compounds cited above as substrates for reaction may contain a halogen element like vinyl chloride and a nitrogen element.

The molecular oxygen-containing gas to be used in this invention does not need to be particularly discriminated. It may be pure oxygen or the nitrogen diluted with an inert gas such as, for example, nitrogen, helium, argon, or carbon dioxide. From the standpoint of safety, controllability, and economy, it is prererably air. The amount of the molecular oxygen to be used can be selected to suit the kinds of the substrates as raw materials for the reaction and the kind of the compound aimed at. It is generally not less than 0.01 mol, preferably in the range of 0.1–100 mols, and more preferably in the range of 1–50 mols, per mol of the substrate.

The reaction temperature is in the range of 0° to 350° C., preferably 25° to 250° C., and more preferably 40° to 180° C. The reaction pressure is selected in the range of normal pressure to 100 atmospheres, preferably normal pressure to 50 atmospheres. The reaction time is selected in the range of 0.1 to 300 hours, preferably in the range of 1 to 48 hours. The pH of the reaction solution is adjusted from time to time by using a buffer solution in consideration of the stability of the catalyst.

Now, this invention will be described more specifically below with reference to working examples. It does not need to be limited to the working examples. The following working examples describe the modes of embodying this invention. Method for preparation of catalyst.

Catalyst A (Synthesis of γ-Keggin type two-defect heteropoly compound substituted with divalent Ru ion)

In an acidified deionized water, γ-Keggin type two-defect heteropoly compound, $K_8[\gamma\text{-SiW}_{10}O_{36}]$ $12H_2O$ (3.0 g, 1.0 m.mol) and $[RuCl_2(p\text{-cymene})_2]$ (0.88 g, 2.0 m.mols) were mixed in their stoichiometric amounts, stirred for 5 minutes, and made to separate a yellow precipitate by addition of an excess amount of tetrabutyl ammonium nitrate (4.1 g, 13 m.mols) This precipitate was filtered, dissolved in 15 ml of acetonitrile, and reprecipitated twice by addition of 300 ml each of water to obtain the product in a purified form. The hydrophobic quaternary tetrabutyl amnonium salt consequently obtained was reprecipited from acetonirile/water for further purification.

Catalyst B (Synthesis of γ-Keggin type two-defect heteropoly compound substituted with divalent Mn ion)

The stoichiometric amount of γ-keggin type two-defect heteropoly compound, $K_8[\gamma\text{-SiW}_{10}O_{36}]12H_2O$ (3.0 g, 1.0 m.mol) was acidified by being dissolved in 30 ml of deionized water. The resultant solution and 0.57 g of manganese nitrate (II) hexahydrate added thereto were together stirred and made to separate a precipitate by addition of 4.1 g (excess) of tetrabutyl ammonium nitrate. This precipitate was filtered, dissolved in 15 ml of acetonitrile, and then reprecipitated twice by the addition of 250 ml each of water to obtain the product in a purified form.

Catalyst C (Synthesis of γ-Keggin type two-defect heteropoly compound substituted with divalent Fe ion)

The stoichiometric amount of γ-Keggin type two-defect heteropoly compound, $K_8[\gamma\text{-SiW}_{10}O_{36}]$ $12H_2O$ (3.0 g, 1.0 m.mol) was acidified by being dissolved in 30 ml of deionized water. The resultant solution and 0.40 g of ferrous chloride tetrahydrate added thereto were together stirred and made to separate a precipitate by addition of 4.1 g (excess) of tetrabutyl ammonium nitrate. This precipitate was filtered, dissolved in 15 ml of acetonitrile, and then reprecipitated twice by the addition of 250 ml each of water to obtain the product in a purified form.

Catalyst D (Synthesis of γ-Keggin type two-defect heteropoly compound substituted with divalent Co ion)

This synthesis was performed by following the procedure for the preparation of Catalyst C while using 0.58 g of cobalt nitrate (II) hexahydrate in the place of the ferrous chloride tetrahydrate.

Catalyst E (Synthesis of γ-Keggin type two-defect heteropoly compound substituted with divalent Ni ion).

This synthesis was performed by following the procedure for the preparation of Catalyst C while using 0.59 g of nickel nitrate (II) hexahydrate in the place of the ferrous chloride tetrahydrate.

EXAMPLE 1

The reaction of epoxidization of cyclooctene was carried out. In a reaction vessel containing 1.5 ml of 1,2-dichloroethane as a solvent and 0.1 ml of acetonitrile, 1 μmol of catalyst A and 19 m mols of cyclooctene were placed and 1 atmosphere of oxygen was further introduced. The reaction vessel was tightly sealed, the interior of the reaction system was kept at 83° C., and then the contents of the reaction vessel were left reacting continuously for 24 hours, 48 hours, and 96 hours meanwhile kept vigorously stirred. At the end of each or the reaction periods mentioned above, the reaction solution was cooled to normal room temperature and the product therein was analyzed by gas chromatography. As the result of the analysis, in the sample of 24-hour reaction, the degree of conversion of cyclooctane was found to be 8.3 mol % and the ratio of selectivity to cyclooctene oxide to be 95 mol %; in the sample of 48-hour reaction, the degree of conversion of cyclooctane was found to be 16.1 mol % and the ratio of selectivity to cyclooctene oxide to be 93 mol %; and in the sample of 96-hour reaction, the degree of conversion of cyclooctane was found to be 21 mol % and the ratio of selectivity to cyclooctene oxide to be 93 mol %. In a separate reaction which was performed under the same conditions for 10 minutes, the analysis showed the degree of conversion of cyclooctane to be 1.5 mol % and the ratio of selectivity to cyclooctene oxide to be 93 mol %. Thus, the induction period of the reaction could not be confirmed.

EXAMPLE 2

The reaction of epoxidization of cyclooctene was carried out by following the procedure of Example 1 while changing the reaction period to 384 hours. The degree of conversion of cyclooctene was found to be 82 mol % and the ratio of selectivity to cyclooctane oxide to be 96 mol %.

EXAMPLE 3

The reaction was performed by following the procedure of Example 1 while using 1-octene in the place of the cyclooctene and changing the reaction period to 48 hours. The degree of conversion of 1-octene was found to be 7 mol % and the ratio of selectivity to 1-octene oxide to be 88 mol %.

EXAMPLE 4

The reaction was performed by following the procedure of Example 1 while using 2-octene in the place of the cyclooctene. The degree of conversion of 2-octene was found to be 16 mol % and the ratio of selectivity to 1-octene oxide to be 83 mol %.

EXAMPLE 5

The reaction was performed by following the procedure of Example 1 while using 1- pentene in the place of the cyclooctene and changing the reaction period to 48 hours. The degree of conversion of 1-pentene was found to be 3 mol % and the ratio of selectivity to 1-pentene oxide to be 69 mol %.

EXAMPLE 6

The reaction was performed by following the procedure of Example 1 while using 2-pentene in the place of the cyclooctene and changing the reaction period to 48 hours. The degree of conversion of 2-pentene was found to be 13 mol % and the ratio of selectivity to 2-pentene oxide to be 45 mol %.

EXAMPLE 7

The reaction was performed by following the procedure of Example 1 while using cyclohexene in the place of the cyclooctene. The degree of conversion of cyclohexene was found to be 24 mol % and the ratio of selectivity to cyclohexene oxide to be 6 mol %.

Control 1

The reaction of epoxidiszation of cyclooctene was carried out by following the procedure of Example 1 while omitting the use of the catalyst A. Even after 96 hours of the reaction, however, no sign of the formation of cyclooctene oxide was detected.

EXAMPLE 8

The reaction of epoxidization of 1-dodecene was carried out. In a reaction vessel containing 1.5 ml of 1,2-dichloroethane as a solvent and 0.1 ml of acetonitrile, 1.5 $\mu$mol of the catalyst A and 20 m mols of 1-dodecene were placed. The reaction vessel was cooled to 0° C. and, with the gas phase part thereof subsequently filled with pure oxygen, tightly sealed, and then immersed in an oil bath kept at 83° C. The contents of the reaction vessel held in the oil bath were left reacting for 24 hours, 48 hours, and 96 hours meanwhile kept vigorously stirred.

At the end of each of the reaction periods mentioned above, the reaction solution was cooled to normal room temperature and the product therein was analyzed by gas chromatography.

As the result of the analysis, in the sample of 24-hour reaction, the yield of 1,2-epoxide dodecane to the charged 1-dodecene was found to be 0.9 mol %; in the sample of 48-hour reaction, the yield of 1,2-epoxide dodecane to the charged 1-dodecene was found to be 4.72 mol %.

Control 2

The reaction of oxidation of 1-dodecene was carried out by following the procedure of Example 8 while using 1.5 $\mu$mols of rhutenium acetonyl acetone in the place of the catalyst C. The yield of 1,2-epoxide dodecane was zero after 24 hours of the reaction. It was 0.05 mol % after 48 hours.

EXAMPLE 9

The reaction of epoxidization of cyclooctene was carried out. In a reaction vessel containing 1.5 ml of 1,2-dichloroethane as a solvent and 0.1 ml of acetonitrile, 1.5 $\mu$mol of the catalyst B and 19 m mols of cyclooctene were placed. The reaction vessel was cooled to 0° C. and, with the gas phase part thereof subsequently filled with pure oxygen, tightly sealed, and then immersed in an oil bath kept at 83° C. The contents of the reaction vessel held in the oil bath were left reacting for 48 hours meanwhile kept vigorously stirred. At the end of the reaction period mentioned above, the reaction solution was cooled to normal room temperature and the product therein was analyzed by gas chromatography. As the result of the analysis, the yield of cyclooctene oxide to the charged cyclooctene was found to be 14.2 mol %.

EXAMPLE 10

The reaction of epoxidization of cyclooctane was carried out by following the procedure of Example 9 while using 1 $\mu$mol of the catalyst C instead. As the result, the yield of cyclooctene oxide to the charged cyclooctene was found to be 8.80 mol % after 48 hours of the reaction.

EXAMPLE 11

The reaction of epoxidization of cyclooctane was carried out by following the procedure of Example 9 while using 1 $\mu$mol of the catalyst D instead. As the result, the yield of cyclooctene oxide to the charged cyclooctene was found to be 14.18 mol % after 48 hours of the reaction.

EXAMPLE 12

The reaction of epoxidization of cyclooctane was carried out by following the procedure of Example 9 while using 1 $\mu$mol of the catalyst E instead. As the result, the yield of cyclooctene oxide to the charged cyclooctene was found to be 11.89 mol % after 48 hours of the reaction.

EXAMPLE 13

The reaction of epoxidization of 1,3-butadiene was carried out. In a reaction vessel containing 1.5 ml of 1,2- dichloroethane as a solvent and 0.1 ml of acetonitrile, 1.5 μmol of the catalyst A and 1 mol of cyclooctene were placed. The reaction vessel was cooled to 0° C. and introduced a blow of 6000 μmols of 1,3-buadiene. The reaction vessel, with the gaseous phase part thereof subsequently filled with pure oxygen, was tightly sealed and immersed in an oil bath kept at 83° C. The contents of the reaction vessel were left reacting for 48 hours meanwhile kept vigorously stirred. At the end of the reaction, the reaction solution was cooled to normal room temperature and the product therein was analyzed by gas chromatography. As the result, the yield of 3,4-epoxibutene was found to be 3.30 mol % and the yield of 1,3-butadiene diepoxide to be 3.4 mol % relative to the charged 1,3-butadiene. The yield of cyclooctene oxide to the cyclooctene was found to be 2.3 mol %.

EXAMPLE 14

The reaction of epoxidization of t-2-butene was carried out by following the procedure of Example 13 while using t-2-butene in the place of 1,3-butadiene. The amount of t-2-butene introduced in this case by blowing was 3000 μmols. After the reaction was continued for 48 hours, the yield of t-2-butene oxide was 2.28 mol % and the yield of c-2-butene oxide was 0.54 mol % relative to the charged butene The yield of cyclooctene oxide relative to the cyclooctene was 18.3 mol %.

EXAMPLE 15

The reaction of epoxidization of c-2-butene was carried out by following the procedure of Example 13 while using c-2-butene in the place of 1,3-butadiene. The amount of c-2-butene introduced in this case by blowing was 6500 μmols. After the reaction was continued for 48 hours, the yield of c-2-butene oxide was 1.49 mol % and the yield of t-2-butene oxide was 3.71 mol % relative to the charged butene. The yield of cyclooctene oxide relative to the cyclooctene was 5.1 mol %.

EXAMPLE 16

The reaction of epoxidization of 1,2-butene was carried out by following the procedure of Example 13 while using 1,2-butene in the place of 1,3-butadiene. The amount of c-2-butene introduced in this case by blowing was 4300 μmols. After the reaction was continued for 48 hours, the yield of 1,2-butene oxide relative to the charged butene was 0.28 mol %. The yield of cyclooctene oxide relative to the cyclooctene was 3.5 mol %.

Control 3

The reaction of epoxidization of 1,3-butadiene, t-2-butene, c-2-butene, and 1,2butene was carried out respectively by following the procedures of Example 13–16. The reactions produced absolutely no corresponding epoxides.

EXAMPLE 17

The reaction of oxidation of cyclohexanol was carried out. In a reaction vessel containing 1.5 ml of 1,2-dichloroethane as a solvent and 0.1 ml of acetonitrile, 1.5 μmol of the catalyst E and 19 m mols of cyclohexanol were placed. The reaction vessel was cooled to 0° C. and, with the gas phase part thereof subsequently filled with pure oxygen, tightly sealed, and then immersed in an oil bath kept at 83° C. The contents of the reaction vessel held in the oil bath were left reacting for 24 hours meanwhile kept vigorously stirred. At the end of the reaction period mentioned above, the reaction solution was cooled to normal room temperature and the product therein was analyzed by gas chromatography. As the result of the analysis, the yield of cyclohexanone to the charged cyclohexanol was found to be 8.3 mol %. The reaction solution was vacuum dried to expel organic substances. The residue of the expulsion was reclaimed as the catalyst E.

EXAMPLE 18

The reaction was carried out by following the procedure of Example 17 while using in the place of the catalyst E the residue obtained by vacuum drying the reaction solution of Example 17 to expel the organic substances. The yield of cyclohexanone was 7.8 mol % and the catalyst could be reused again.

EXAMPLE 19

The reaction of oxidation of ethylene glycol was carried out. In a reaction vessel containing 1.5 ml of 1,2-dichloroethane as a solvent and 0.1 ml of acetonitrile, 1.5 μmol of the catalyst D and 19 m mols of ethylene glycol were placed. The reaction vessel was cooled to 0° C. and, with the gas phase part thereof subsequently filled with pure oxygen, tightly sealed, and then immersed in an oil bath kept at 83° C. The contents of the reaction vessel held in the oil bath were left reacting for 24 hours meanwhile kept vigorously stirred. At the end of the reaction period mentioned above, the reaction solution was cooled to normal room temperature and the product therein was analyzed by gas chromatography. As the result of the analysis, the yield of glycolic acid was found to be 2.08 mol % and the yield of formaldehyde to be 3.2 mol % relative to the charged ethylene glycol.

Control 4

The reaction of oxidation of ethylene glycol was carried out by following the procedure of Example 19 while using 1.5 μmol of cobalt acetate (II) tetrahydrate as a catalyst instead. As the result, the yield of glycolic acid was found to be 1.72 mol % and the yield of formaldehyde to be 4.3 mol % after 24 hours of the reaction. Thus, the reaction formed glycolic acid in low yield and tended to induce decomposition.

EXAMPLE 20

The reaction of oxidation of allyl alcohol was carried out by following the procedure of Example 17 while using 9 mmols of allyl alcohol in the place of cyclohexanol, using the catalyst A in the place of the catalyst E, and chanting the reaction temperature to 70° C. As the result, the yield of acrolein relative to the charged allyl alcohol was found to be 6.0 mol % after 24 hours of the reaction.

EXAMPLE 21

The reaction of oxidation of 2,3-butane diol was carried out by following the procedure of Example 17 while using 2,3-butane diol in the place of the ethylene glycol. As the result of 24 hours of the reaction, the yield of 3-hydroxy-2-butanone relative to the charged 2,3-butane diol was found to be 0.9 mol %.

EXAMPLE 22

The reaction of oxidation of propionaldehyde was carried out. In a reaction vessel containing 1.5 ml of 1,2- dichloroethane as a solvent and 0.1 ml of acetonitrile, 1.5 μmol of the catalyst C and 19 m mols of propionaldehyde were placed. The reaction vessel was cooled to 0° C. and, with the gas phase part thereof subsequently filled with pure oxygen, tightly sealed, and then immersed in an oil bath kept at 83° C. The contents of the reaction vessel held in the oil bath were left reacting for 24 hours meanwhile kept vigorously stirred. At the end of the reaction period mentioned above, the reaction solution was cooled to normal room temperature and the product therein was analyzed by gas chromatography. The yield of propionic acid was found to be 45.7 mol % relative to the charged propionaldehyde.

Control 6

The reaction of oxidation of propionaldehyde was carried out by following the procedure of Example 22 while using 1.5 μmol of ferric chloride (II) tetrahydrate instead as a catalyst. As the result, the yield of propionic acid after 24 hours of the reaction was found to be 19.9%.

EXAMPLE 23

The reaction of oxidation of methacrolein was carried out. In a reaction vessel containing 1.5 ml of 1,2-dichloroethane as a solvent and 0.1 ml of acetonitrile, 1.5 μmol of the catalyst B and 19 m mols of methacrolein were placed. The reaction vessel was cooled to 0° C. and, with the gas phase part thereof subsequently filled with pure oxygen, tightly sealed, and then immersed in an oil bath kept at 83° C. The contents of the reaction vessel held in the oil bath were left reacting for 24 hours meanwhile kept vigorously stirred. At the end of the reaction period mentioned above, the reaction solution was cooled to normal room temperature and the product therein was analyzed by gas chromatography. As the result, the yield of methacrylic acid was found to be 4.10 mol % relative to the charged methacrolein.

The entire disclosure of Japanese Patent Application No. 11-366542 filed on Dec. 24, 1999 and No. 2000-340760 filed on Nov. 8, 2000 including specification, claims and drawing and summary are incorporated herein by reference in its entirety.

What is claimed is:

1. A method for the production of an oxygen-containing organic compound, which comprises oxidizing an olefin, an alcohol, or an aldehyde catalyzing thereof with a molecular oxygen-containing gas in the presence of a catalyst formed of a polyoxo metalate substituted with a divalent transition metal cation.

2. A method for the production of an oxygen-containing organic compound, which comprises oxidizing an olefin, an alcohol, or an aldehyde by catalyzing thereof with a molecular oxygen-containing gas in the presence of a catalyst formed of a polyoxo metalate substituted with two transition metal cations, said cations being displaced with mutually adjoining transition metal cations.

3. A method for the production of an oxygen-containing organic compound, which comprises oxidizing an olefin, an alcohol, or an aldehyde by catalyzing thereof with a molecular oxygen-containing gas in the presence of a catalyst formed of a heteropoly silicotungstate substituted with a transition metal cation possessed of a γ-type Keggin structure.

4. A method according to claim 1, wherein said transition metal cation is at least one divalent cation selected from the group consisting of manganese, iron, cobalt, and nickel.

5. A method according to claim 2, wherein said transition metal cation is at least one divalent cation selected from the group consisting of manganese, iron, cobalt, and nickel.

6. A method according to claim 3, wherein said transition metal cation is at least one divalent cation selected from the group consisting of manganese, iron, cobalt, and nickel.

7. A method according to claim 1, wherein said transition metal cation is at least one divalent cation selected from among noble metal ions.

8. A method according to claim 2, wherein said transition metal cation in at least one divalent cation selected from among noble metal ions.

9. A method according to claim 3, wherein said transition metal cation is at least one divalent cation selected from among noble metal ions.

10. A method according to claim 7, wherein said metal cation is a ruthenium ion.

11. A method according to claim 8, wherein said metal cation is a ruthenium ion.

12. A method according to claim 9, wherein said metal cation is a ruthenium ion.

\* \* \* \* \*